United States Patent [19]

Barker et al.

[11] Patent Number: 5,272,094

[45] Date of Patent: Dec. 21, 1993

[54] ISOLATION OF COMPONENTS FROM BIOLOGICAL SPECIMENS VIA MATRIX SOLID PHASE DISPERSION

[75] Inventors: Steven A. Barker; Austin R. Long, both of Baton Rouge, La.

[73] Assignee: Board of Supervisors of Louisiana State University and Agricultural and Mechanical College, Baton Rouge, La.

[21] Appl. No.: 26,275

[22] Filed: Mar. 4, 1993

Related U.S. Application Data

[63] Continuation of Ser. No. 893,903, Jun. 4, 1992, abandoned, which is a continuation of Ser. No. 347,349, May 4, 1989, abandoned.

[51] Int. Cl.$^5$ .......................................... G01N 33/543
[52] U.S. Cl. ............................... 436/518; 436/174; 436/524; 436/527; 436/528; 435/274
[58] Field of Search ........ 436/174, 518, 524, 527-528; 435/262, 274

[56] References Cited

U.S. PATENT DOCUMENTS 4,680,120  7/1987  Ramsden et al. ................. 436/178

OTHER PUBLICATIONS

Calton et al. in "Manual of Industrial Microbiology and Biotechnology", Demain, Solomon (eds), pp. 436-445, 1986, ASM.

Lewis et al., "Determination of Nicarbazin in Chicken Tissues by Liquid Chromatography and Confirmation of Identity by Thermospray Liquid Chromatography/Mass Spectrometry," J. Assoc. Off. Anal. Chem., vol. 72, No. 4, pp. 577-581 (1989).

Gallicano et al., "Simultaneous Liquid Chromatographic Screening of Five Coccidiostats in Chicken Liver," J. Assoc. Off. Anal. Chem., vol. 71, No. 1, pp. 48-50 (1988).

Verzele, et al., "Quality Criteria and Structure of Silica Gel Column Packing Material", J. Chrom., vol. 329, pp. 351-357 (1985).

Dewaele, et al., "Influence of the Particle Size Distribution of the Packing Material in Reversed-Phase High-Performance Liquid Chromatography", J. Chrom., vol. 260, pp. 13-21 (1983).

Parks, "Rapid Procedure for Determination of Nicarbazin Residues in Chicken Tissues," J. Assoc. Off. Anal. Chem., vol. 71, No. 4, pp. 778-780 (1988).

Epstein et al., "Organotin Residue Determination in Poultry and Turkey Sample Survey in the United States," J. Agric. Food Chem., vol. 39, No. 5, pp. 917-921 (1991).

Boison et al., "Determination of Penicillin G Residues in Edible Animal Tissues by Liquid Chromatography," J. Assoc. Off. Anal. Chem., vol. 74, No. 3, pp. 497-501 (1991).

Chuaqui-Offermanns et al., "An HPLC Method to Determine o-Tyrosine in Chicken Meat," J. Agric. Food Chem., vol. 39, No. 2, pp. 300-302 (1991).

Lebo et al., "Determination of Monocyclic and Polycyclic Aromatic Hydrocarbons in Fish Tissue," J. Assoc. Off. Anal. Chem., vol. 74, No. 3, pp. 538-544 (1991).

(List continued on next page.)

Primary Examiner—Lyle A. Alexander
Attorney, Agent, or Firm—Llewellyn A. Proctor; John H. Runnels

[57] ABSTRACT

A process is disclosed for the isolation of a compound such as a drug or drug metabolite from a biological specimen such as a tissue. The specimen to be analyzed is ground with a particulate solid to which is bound a lipophilic material, in order to disrupt and disperse the components of the specimen into the lipophilic material or into the particulate solid. The solid on which the specimen is dispersed may then be directly used as a column packing material without further clean-up. The drug or other compound of interest may be eluted from the column with one or more solvents, and then analyzed.

31 Claims, No Drawings

OTHER PUBLICATIONS

Momplaisir et al., "Determination of Arsenobetaine, Arsenocholine, and Tetramethylarsonium Cations in Seafoods and Human Urine by High-Performance Liquid Chromatography-Thermochemical Hydride Generation-Atomic Absorption Spectrometry," J. Agric. Food Chem., vol. 39, No. 8, pp. 1448–1451 (1991).

Chaput, "Simplified Multiresidue Method for Liquid Chromatographic Determination of N-Methyl Carbamate Insecticides in Fruits and Vegetables," J. Assoc. Off. Anal. Chem., vol. 71, No. 3, pp. 542–546 (1988).

Ali, "Determination of N-Methylcarbamate Pesticides in Liver by Liquid Chromatography," J. Assoc. Off. Anal. Chem., vol. 72, No. 4, pp. 586–592 (1989).

LeVan et al., "Liquid Chromatographic Method for Multiresidue Determination of Benzimidazoles in Beef Liver and Muscle: Collaborative Study," J. Assoc. Off. Anal. Chem., vol. 74, No. 3, pp. 487–492 (1991).

Tai et al., "Determination of Thiabendazole, 5-Hydroxythiabendazole, Fenbendazole, and Oxfendazole in Milk," J. Assoc. Off. Anal. Chem., vol. 73, No. 3, pp. 368–373 (1990).

Roybal et al., "Determination of Gentian Violet, Its Demethylated Metabolites, and Leucogentian Violet in Chicken Tissue by Liquid Chromatography with Electrochemical Detection," J. Assoc. Off. Anal. Chem., vol. 73, No. 6, pp. 940–946 (1990).

Aerts, et al., "Liquid Chromatographic Determination of Chloramphenicol Residues in Meat: Interlaboratory Study," J. Assoc. Off. Anal. Chem., vol. 72, No. 4, pp. 570–576 (1989).

ISOLATION OF COMPONENTS FROM BIOLOGICAL SPECIMENS VIA MATRIX SOLID PHASE DISPERSION

ACKNOWLEDGMENT

The work leading to this invention was sponsored by the Food and Drug Administration (Contract No. FD-V-00235 and 5V01-FD-01319), and accordingly the U.S. Government may have rights thereunder.

This application is a continuation of copending application Ser. No. 07/893,903, filed Jun. 4, 1992, now abandoned which is a continuation of prior application Ser. No. 07/347,349, filed May 4, 1989, now abandoned.

FIELD OF THE INVENTION

This invention relates to a process for the isolation, for identification, of compounds such as drugs, and drug metabolites from biological specimens, notably tissues. In particular, it relates to a process for the dissolution and dispersion upon solids of a biological specimen, or tissue, which may contain drugs, and drug metabolites, and the multiresidue extraction of the dissoluted biological specimen, or tissue.

BACKGROUND

Techniques are known for the analysis of compound such as drugs, and drug metabolites, such as are employed in screening for drugs of abuse in urine samples. The suspect chemical compounds are isolated by specific or generic counter-current extraction methods according to chemical class, and then analyzed. The analysis is made generally by such techniques as thin layer chromatography, immunoassay, gas chromatography using nitrogen/phosphorous or election capture detection, high pressure liquid chromatography (HPLC) using fluoresense, ultra violet or electrochemical detection, and the like. It should be expected that a compound such as a drug, or drug residue, extracted from a biological specimen, or tissue could be analyzed in similar manner if extracts of the biological specimens, or tissues, of adequately high purity could be prepared.

The preparation however of a high purity extract from, e.g., tissues presents a much more formidable problem than the manipulation of a urine matrix. It is well known that interfering substances abound in tissues, and that these substances must be eliminated from the extract before analysis is possible. For example, in thin layer chromatography, interfering substances must be absent, and lipid concentration must be reduced to levels which will prevent streaking of a sample. For radioimmunoassay analysis, e.g., isolation of the compounds of interest from the tissue matrix is required, as well as the removal of endogenous substances which produce false positive results. For gas chromatography and high pressure liquid chromatography there are a number of compounds that must be eliminated because they produce interfering peaks which make it difficult, or impossible, to detect trace levels of drugs and their metabolites.

Classical methods for tissue extraction involve homogenation of the tissues in an aqueous medium, multiple extractions and centrifuging for removal of debris, precipitation of proteins by adjustment of pH with acids, or bases, or by the addition of salts. Classical methods for the isolation of a compound such as a drug, or drug metabolite, from a matrix thus generally requires (1) mincing and/or mechanical homogenization of the tissue in an aqueous solvent; (2) addition of acids, bases, or salts to precipitate protein and remove debris; (3) centrifugations; (4) transfer of the supernatant and adjustment of pH; (5) counter-current extraction of the sample, often leading to intractable emulsions; and (6) back-extraction of the sample to assist in purification of the sample. Often also, homogenization in and repeated extraction of tissues by organic solvents are required, these generating large volumes of solvents which must be evaporated; and usually back-extracted. The necessity for multiple counter-current extractions of the isolated supernatant requires considerable time, and can adversely affect the accuracy of the analysis. Unfortunately such manipulations are burdensome per se, and invariably lead to emulsion formation and the necessity of further slow manipulations of the samples.

Solid phase extraction, SPE, technology has been used extensively over the past decade, but this technology has provided only a partial solution to the problem. With this technique an SPE column is packed with various materials; usually polymer-bound beads of various sizes. A supernatant of a homogenized, manipulated specimen of a tissue suspected to contain a compound, drug, or drug residue, is added to the SPE column, and this is followed by elution with a solvent, or solvents, to isolate a specific compound, drug, or class of drugs. The SPE process eliminates emulsion formation and lessens the volumes of solvent required to isolate a given drug, or compound, as contrasted with classical methods. Prior to passage of the sample through the SPE column however, homogenation of the tissue and manipulations of the specimen to remove cell debris is required. Often also it is required to remove the proteins and lipids. The removal of the cell debris, and as well the proteins and lipids, prevents plugging of the column and overloading the polymer phase. Accordingly, after homogenizing the tissue the homogenized specimen is pelletized by centrifugation, and the proteins precipitated. Thus, in this procedure most of the classical manipulations are still required, and it is necessary that the homogenized tissue specimen be pelletized in an aqueous medium prior to extraction. The necessity of having to pelletize the specimen is particularly disadvantageous in that entrained or electrostatically compounds, drugs, or drug residues, are sometimes lost. Moreover less than the whole of the tissue specimen is extracted in the SPE column. For these reasons, inter alia, the isolation of compounds such as drugs, and drug residues, from the matrices of biological specimens, or tissue matrices, via known solid phase extraction techniques have left much yet to be desired.

OBJECTS

It is, accordingly, an object of this invention to provide a process which will dispose of these and other problems associated with the handling and manipulating of biological specimens, and tissues for analysis of compounds such as drugs.

In particular, it is an object to provide a process which will eliminate the need to homogenize, centrifuge, precipitate proteins, adjust pH, or manipulate a biological specimen, or tissue sample as required via classical techniques in preparing a specimen for introduction into an SPE column.

A further and more specific object is to provide a process for the isolation of a compound such as a drug, or drugs, and their metabolites, from biological specimens, or tissues, by dissolving or dispersing the biological specimens, or tissues onto a solid phase support to provide a semi-dry, easy to handle column packing material from which the individual compound(s) drug(s), or drug residue(s), can be isolated.

THE INVENTION

These objects and others are achieved in accordance with this invention embodying a process wherein a biological specimen, or tissue to be screened for a drug(s), or drug metabolite(s), is contacted with, and directly absorbed, dissolved, or dispersed onto a particulate polymer bonded solid support to yield a semi-dry tissue-coated matrix. The semi-dry tissue coated particulate solid support is then contacted with a solvent, or solvents, to elute the compound(s) drug(s), or drug metabolite(s), from the biological specimen, or tissue. Preferably, the semi-dry particulate solid on which the biological specimen, or tissue is dispersed is introduced into a column to form a bed, and the bed of semi-dry coated particulate solid is then contacted and washed with a solvent, or solvents, to elute the compound(s) drug(s), or drug residue(s), therefrom. This technique eliminates any need to homogenize the biological specimen, or tissue, to centrifuge, precipitate proteins, or adjust the pH of a homogenized biological specimen, or tissue, prior to addition of the specimen to the column. The entire biological specimen, or tissue is exposed to extraction, and losses of a compound such as a drug(s), or rug residue(s), due to the pelletization of the biological specimen, or tissue as required in conventional SPE technology are avoided. The eluted compound, drug, or drug residue, can be analyzed conventionally after extraction in this manner, e.g. as by thin layer chromatography, immunoassay, gas chromatography, or high pressure liquid chromatography.

In the initial preparation of the biological specimen, or tissue to be analyzed for a compound such as a drug, or drug residue, a measured quantity of the whole raw specimen, without preparation is admixed with the particulate polymer bonded solid support, and ground, suitably within a mortar and the admixture ground under a pestle, until the biological specimen, or tissue is completely solubilized within the polymer bonded particulate solid to form a semi-dry coated powder, e.g., a tissue coated powder. The cellular structure is completely disrupted and cell membranes dissolved by the grinding operation, this allowing access to internal cellular components which are dissolved along with cell membranes onto the solid support. Polymer-bound beads, or beads to which there is bound a lipid solubilizing polymeric material, are a preferred type of particulate polymer bonded solid support. The lipophilic polymer attached to the beads, or other solid support, can be straight chain, branched chain or cyclic, saturated or unsaturated, substituted or unsubstituted, and the carbon chain of the attached polymer moieties can range in length up to about 30 carbon atoms, or more. The lipophilic polymer phases thus range from reverse-phase ($C_3$, $C_8$, $C_{18}$) to normal phase (polar; $SO_3$, $NH_2$, CN, etc.). Such materials are available in the nature of SPE and HPLC column packing materials composed of, e.g. octadecylsilane polymer bound to silica beads ($C_{18}$). The solid support is generally a neutral material, though its specific composition is not critical. It can be inorganic or organic, e.g., alumina, silica, or solid or semi-solid polymer. It is essential only that the lipid solubilizing characteristics of the surface attached lipophilic polymer be retained. Thus, e.g., by adding whole tissues (0.5 g) to $C_{18}$ packing (2.0 g) in a mortar and gently grinding the material for about one-half minute, there is obtained a near-homogenous mix of tissue cell membranes "dissolved" into the solid phase packing material. The semi-dry powder is then packed into a column from which compounds may be eluted based on their solubilities in the polymer-tissue matrix. Elution profiles have shown that several classes of compounds or drugs can be isolated from a single tissue specimen, with different classes being isolated in each of the different eluting solvents. For example, elution with hexane and benzene can isolate the organophosphates; elution with methylene chloride, the sulfonamides; elution with ethyl acetate, the benzimidazoles; elution with methanol, the beta-lactam antibiotics; and elution with water, cellular proteins, DNA and RNA.

In some instances it may be desirable to add an acid, base or salt modifier to effect elution or the isolation of a compound during the elution step. Exemplary acids, which can modify the elution characteristics of a compound such as a drug, or drug Metabolite, are organic acids such as malic, formic, citric and the like, or inorganic acids such as hydrochloric, nitric, sulfuric and the like. Exemplary bases are, e.g., sodium hydroxide, ammonium hydroxide, pyridine, methylamine or the like; and exemplary salts are, e.g., sodium chloride, potassium chloride, ethylenediamine, ethylenediamine tetraacetate (EDTA) and the like. An admixture of oxylic acid and EDTA will, e.g., change the elution characteristics of the tetracyclines.

Each tissue provides a different matrix, having unique elution properties. Some characterization is required to determine the best, or more ideal polymer for dissolving a given tissue specimen, e.g., the best ratios of $C_{18}$ to tissue. Such technique nonetheless can be applied as a generic method for the isolation of drugs, and drug metabolites, of natural compounds from tissues. Generally, no post clean-up of a sample is required prior to analysis.

The following non-limiting examples are exemplary of, and bring out the more salient features of the invention. Except as otherwise specified all parts are given in terms of weight units.

The examples immediately following show that tissues can be blended with a polymeric phase bound to a solid support to obtain a semi-dry material which can be employed as a column packing material from which compounds such as drugs can be isolated in stepwise fashion based on the solubility characteristics of the drugs or other compounds in this matrix. The applicability of this approach for multidrug residue extraction from a single sample is demonstrated for compounds representing the organophosphate, benzimidazole anthelmentic and beta-lactam antibiotic drug classes.

EXAMPLES 1-14

Bulk C-18 (octadecylsilane coated silica bead, 40 um, end capped, 18% load) SPE column packing material was obtained from Analytichem International, Harbor City, Calif. The material was washed prior to use by placing 24 g of the packing in an emptied 50 ml Chem-Elut column (Analytichem International), attaching the column to a vacuum box and sequentially adding 50 ml each of HPLC grade hexane, benzene, ethyl acetate and methanol to remove contaminants inherent in manufacture. Tissues (bovine muscle) were obtained from commercial food markets and were kept frozen at $-5°$ C.

until utilized. Thawed tissues (0.5 g) were injected (10 ul syringe) with drugs dissolved in dimethyl sulfoxide or dimethyl formamide at various concentrations for analysis. Blank samples were injected with the corresponding solvents used to dissolve the drug standards.

The following compounds were examined: 1) organophosphates (phenthion, crufomate, coumaphos and famfur); 2) benzimidazole anthelmintics (fenbendazole, FBZ: oxfendazole, FBZSO; sulfonyl FBZ, FBZSO$_2$; p-hydroxy-FBZ, FBZOH; mebendazole, MEB; thiabendazole, THI; and albendazole, ALB); and 3) beta-lactam antibiotics (penicillin, ampicillin and cephapirin). The concentrations examined are shown in Table 1.

SAMPLE PREPARATION

Samples were prepared in the following manner: Tissue blanks or spiked tissues (0.5 g) were added to 2.0 g of prewashed C-18 packing material in a glass mortar. The sample was gently blended with a glass pestle for 30 seconds to produce a semi-dry, homogenous appearing material. This was added to a syringe barrel-column (10 ml) containing a frit (0.45 um) and 0.50 g of clean C-18 packing at the bottom. Clean packing (0.25 g) was added to the top of the column and the column was lightly tamped to remove air pockets. A retainer was placed on top of the material and a syringe plunger was used to compress the sample to a volume of 4 ml. A 100 ul disposable pipette tip was attached to the end of the column and the column was placed in a rack, ready for elution. The following elution profile, collecting each fraction separately, was performed; hexane, benzene, ethyl acetate and methanol (8 ml of each, respectively). The four fractions were evaporated to dryness under dry nitrogen and an appropriate solvent was added to solubilize the residue; 1) hexane and benzene fractions; 500 ul n-hexane; 2) ethyl acetate fraction; 50 ul acetonitrile and 450 ul of 0.05N phosphoric acid; and 3) methanol fraction; 500 ul of 0.05N phosphoric acid. The resulting suspension was centrifuged (5 min. at 2100 rpm) and the supernatant was filtered through a 0.45 um (BioRad) disposable filter. The compounds detected in each fraction are shown in Table 1.

SAMPLE ANALYSIS

Organophosphates; Analyses were conducted by gas chromatography (GC, Varian Vista 6000; column, DB-5 (J & W Scientific), 25M by 0.25 mm id, 0.25 mm coating. Temperature program of 150° C. for 1 min., increasing 10° C./min. to 300° C. and holding for 2 min. Splitless injection with the purge function was activated at 0.75 min. post injection. Injection port temperature of 250° C. Detection was accomplished using a nitrogen/phosphorus detector (NPD); 300° C., 6.0 mV at 10–12 sensitivity setting).

Benzimidazoles; Analyses were conducted by high pressure liquid chromatography with photo diode array detection (Hewlett Packard 1090. Column; octadecylsilane, 12.5 cm by 0.5 cm id, 10 um particle size (Varian Associates, MCH-10). Solvent system; isocratic (0.75 ml/min.), 0.05N phosphoric acid: acetonitrile (67:33, v/v). Column temperature of 45° C.). Detection and quantitation were conducted at 290 nm (20 mm band width, reference spectrum range of 200–350 mm). Full UV spectra were used to determine, in part, the identity of each benzimidazole and the purity of each peak.

Beta Lactams; Analyses were conducted as described above using a detection wavelength of 230 nm and a solvent system (isocratic, 1.0 ml/min.) of 0.05N phosphoric acid: acetonitrile (80:20) and a column temperature of 35° C.

Recoveries for all compounds were determined from comparison of the data obtained from extracted samples to the data obtained by direct analysis of each compound at the respective concentrations without extraction.

TABLE 1

List of compounds examined, range of concentrations (ug/g) analyzed, eluting solvent wherein drug was obtained, correlation coefficients (r, + or − standard deviation. SD, 6 points) for standard curves, recoveries (calculated for all concentrations. + or − SD, inter- and intra-assay variabilities (mean of n determinations).

| COMPOUND | FRACTION COLLECTED | CONCENTRATION (ug/g) RANGE EXAMINED | r ± SD n = 4 | RECOVERY ± SD n = 20 | INTERASSAY VARIABILITY n = 20 | INTRAASSAY VARIABILITY n = 5 |
|---|---|---|---|---|---|---|
| Fenthion | Hexane | 0.1–2 | .997 ± .003 | 85.62 ± 7.50 | 8.40 | 3.01 |
| Coumaphos | Hexane | 0.1–2 | .998 ± .007 | 76.57 ± 7.87 | 20.62 | 7.08 |
| Famfur | Benzene | 0.4 | — | 82.10 ± 8.78 | 10.70 | 5.50 |
| Crufomate | Benzene | 0.1–2 | .992 ± .006 | 93.64 ± 6.38 | 6.82 | 6.05 |
| Thiabendazole | ETOAC | 0.2–4.0 | .9975 ± .0019 | 63.82 ± 9.57 | 6.91 | 2.74 |
| SO Metab | ETOAC | 0.2–4.0 | .9912 ± .0019 | 82.86 ± 9.48 | 7.08 | 3.79 |
| OH Metab | ETOAC | 0.2–4.0 | .9900 ± .0081 | 68.35 ± 10.5 | 13.31 | 8.18 |
| SO$_2$ Metab | ETOAC | 0.2–4.0 | .9962 ± .0009 | 85.67 ± 15.04 | 5.01 | 3.01 |
| Mebendazole | ETOAC | 1.0 | — | 63.01 ± 4.24 | 8.10 | 4.37 |
| Albencazole | ETOAC | 0.2–4.0 | .9975 ± .0017 | 73.92 ± 7.99 | 3.07 | 3.95 |
| FBZ | ETOAC | 0.2–4.0 | .9842 ± .0099 | 73.97 ± 11.82 | 7.29 | 5.65 |
| Cephapirin | Methanol | 0.2–5 | .992 ± .007 | 72.37 ± 26.48 | 10.23 | 6.90 |
| Penicillin | Methanol | 0.2–5 | .994 ± .005 | 86.29 ± 6.12 | 17.88 | 4.99 |
| Ampicillin | Methanol | 2.0 | — | 59.75 ± 9.75 | 27.82 | 8.61 |

RESULTS

Table 1 shows the levels of each compound examined, the fraction in which it was obtained, the recoveries for each compound, correlation coefficients of standard curves and the inter- and intraassay variability obtained for analyses so conducted. The organophosphates phenthion and coumaphos were detected in the hexane fraction, whereas the compounds crufomate and famfur were observed to elute in the benzene fraction. Famfur was used as an internal standard in these studies, being spiked in all samples prior to extraction at a level of 0.4 ug/g and was added as an external standard for the analysis of the hexane fraction.

The presence of a small quantity of lipid was noted in the hexane and benzene fractions but its presence did not interfere with the analyses of the organophosphates in any manner. Analyses of the hexane and benzene fractions by HPLC gave no indication of the presence of even trace levels of the benzimidazole anthelmintics. No further sample cleanup was required for the analysis of the organophosphates in these fractions.

Analysis of the ethyl acetate fraction by HPLC showed that all of the benzimidazoles examined here are eluted in this fraction. The compound mebendazole (MEB) served as an internal standard for these analyses. Under the conditions used no interfering substances were noted, eliminating the need for back-extraction or further cleanup of the sample prior to analysis. Analysis of the ethyl acetate fraction by the HPLC method described for beta-lactams gave no indication that the beta-lactams are eluted in this fraction. Elution of the columns with methanol yielded, upon evaporation, a white residue which, upon testing with ninhydrin, was determined to consist mainly of proteins. Addition of 0.05N phosphoric acid, vortexing and centrifugation of the resulting suspension produced a relatively clean supernatant, devoid of much of the proteinaceous material. Analysis of the resultant samples by HPLC indicated that, for the analysis of penicillin and cephapirin, using ampicillin as an internal standard, no further sample cleanup was necessary. Analysis of the methanol extract by the method for benzimidazoles gave no evidence for the presence of any of the benzimidazoles in this fraction.

Classical methodologies have on occasion employed the use of surfactants or detergents to disrupt or, otherwise, dissolve tissue cell membranes so as to liberate internal components of cells and to remove protein and other cellular components from a lipid membrane matrix. The use of detergents however often leads to their interfering in the isolation procedure or subsequent analysis and additional steps must often be taken to assure their removal, which can be a laborious task. Not so however in the practice of the present invetnion. The present technique requires the use of a lipid solubilizing material to disrupt cell membranes and to, essentially, disperse tissues, but with the requirement that the dispersing agent be bound to a solid support. The cell membrane is disrupted through solubilization of the component phospholipids and cholesterol into the C-18 polymer matrix, with more polar substituents directed outward, perhaps forming a hydrophilic outer surface on the bead. The cells are in a sense turned inside-out to form an inverted membrane with the polymer bound to the solid support. The process may thus create a pseudo-ion exchange/reverse phase for the separation of added components. Thus, the C-18 polymer would be modified by cell membrane phospholipids, interstitial fluid components, intracellular components, cholesterol, etc., and to some degree would possess elution properties that would be dependent on the tissue used, the ratio of C-18 to tissue employed and the elution profile performed.

Examinations of the blended materials by scanning electron microscopy indicate that complete disruption of the cells does occur and that this process of disruption may be further modified by the use of a solvent to blend the tissues.

The blending of tissue with C-18 coated silica beads by the use of a mortar and pestle proceeds rapidly and smoothly, producing a semi-dry, homogenous appearing material. This has been observed to be the case with either fat, liver or muscle tissues. The mechanical forces applied during homogenization may be sufficient to lead to fracturing of some of the beads. However, to whatever degree this may occur, it does not appear to affect the flow of solvent through the column or lead to active sites wherein compounds may be lost.

The following examples describe the isolation of sulfonamides from pork muscle, and subsequent liquid chromatographic analysis of the isolated sulfonamides. Sulfonamides are broad spectrum antibiotics widely used in the livestock producing industry. The use of antibiotics as chemotherapeutic agents in animal production has increased in the last decade. These drugs are an integral part of the livestock production industry and function to prevent disease and/or increase feed efficiency. However, residues of these drugs in foods derived from treated animals could pose a health threat to consumers and the constant exposure of some microorganisms to these drugs may manifest itself in the development of drug resistant strains. Regulatory agencies have established withdrawal periods for such drugs for animals treated prior to slaughter, as well as maximal residue levels in foods, to minimize their impact.

EXAMPLES 15-22

Pork muscle tissue was obtained from a local market. Two (2) grams of C-18 packing were placed into a glass mortar and pork tissue (0.5 gm) was placed onto the C-18. Sulfonamide standards (10 ul, 3.125-100 ug/mL) and internal standard sulfamerazine (10 uL, 10 ug/mL) were injected (10 ul syringes) into the tissue and were allowed to stand for 2 min. Blank tissues were prepared similarly, except that 20 uL of methanol containing no sulfonamides were added. The tissues were then blended into the C-18 material with a glass pestle until a homogenous mixture was observed (30 sec.). The resultant C-18/tissue matrix was transferred to a 10 mL syringe barrel containing 2 filter paper discs. Two filter paper discs were placed on the column head and the column was compressed to a final volume of 4.5 mL using a syringe plunger which had the rubber end and pointed plastic portion removed. A pipette tip (100 uL) was placed on the column outlet to increase the residence time of the eluting solvents on the column.

The column was first washed with HPLC grade hexane (8 mL) by gravity flow. When flow had ceased excess hexane was removed by applying positive pressure (pipette bulb) to the column head until any remaining hexane was eluted. Sulfonamides were then eluted with methylene chloride (DCM, 8 mL) as described above. The DCM extract was dried under a steady flow of dry nitrogen gas. To the dry residue were added 0.1 mL of methanol and 0.4 mL of 0.05N $H_3PO_4$. The sample was sonicated (5-10 min.) to disperse the residue, which resulted in a suspension. The resultant suspension was transferred to a microcentrifuge tube and centrifuged at $10,000 \times g$ for 10 min. The supernatant was filtered through a 0.45 micron filter (Micro Prep-Disc, Bio-Rad Laboratories, Richmond, Calif.) and an aliquot (20 uL) of this solution was analyzed by HPLC.

HPLC ANALYSIS

Analysis of standard and extracted sulfonamides were conducted utilizing a Hewlett Packard HP1090 (HP 79994A HPLC Chemstation) liquid chromatograph equipped with a photodiode array detector set at 270 nm (bandwidth 20 nm) and a sensitivity of 0.1 mAUFS utilizing a reference spectrum range of 200-350 nm. The solvent system was a 70:30 (v/v) ratio of 0.05N $H_3PO_4$ to acetonitrile at an isocratic flow rate of 1 mL/min. A reversed phase (octadecylsilyl derivatized silica, ODS)

column (30 cm×4 mm, Varian MCH-10), maintained at 40° C., was used for all determinations.

Peak area ratio (PAR) standard curves of standards and sample extracts were obtained by dividing intregration areas of generated peaks of each compound by that of the internal standard. Percentage recoveries were determined by comparing PAR's of extracted spiked samples to those of pure standards run under identical HPLC conditions. Interassay variability was determined as the mean of the standard error of the mean PAR's of 5 replicate standard curves. Intra-assay variability was determined by the standard error of the mean PAR's of 5 replicates of the same samples.

Table 2 gives the compounds examined, concentrations anaylyzed, standard curve correlation coefficents (+ or − standard deviation), percentage recoveries and inter- and intra-assay variabilities of the sulfonamides isolated from spiked pork tissue.

sulfamethoxazole, sulfisoxazole and sulfadimethoxine in a milk-based infant formula. Blank or sulfonamide spiked infant formula samples were blended with octadecylsilyl derivatized silica (C-18) packing material. A column made from the C-18/infant formula matrix was first washed with hexane following which the sulfonamides were eluted with methylene chloride.

The data compound, compound concentrations, correlation coefficients (+ or − standard deviation), percentage recovery, inter- and intra-assay variability of the sulfonamides obtained when the eluates were analyzed by liquid chromatography are given in Table 3, HPLC analysis was conducted as described with regard to Examples 15–22.

TABLE 3

INFANT FORMULA

Compounds studied, (concentrations 62.5, 125, 250, 500, 1000 and 2000 ng/ml; 200 ng/mL of sulfamerazine as internal standard; 20 uL injection), correlation coefficients (+ or − standard deviation; SD), percentage recovery, inter- and intra-assay variablity of the 7 sulfonamides isolated from spiked infant formula samples. (x = mean).

| COMPOUND | CORRELATION r ± SD, n = 5 | % RECOVERY x ± SD, n = 30 | INTERASSAY VARIABILITY %, n = 30 | INTRA-ASSAY VARIABILITY %, n = 5 |
|---|---|---|---|---|
| Sulfathiazole | 0.9973 ± .0016 | 75.91 ± 11.12 | 9.58 ± 3.23 | 3.15 |
| Sulfadiazine | 0.9972 ± .0018 | 99.62 ± 5.31 | 9.71 ± 3.47 | 6.65 |
| Sulfamerazine | Internal Standard | 92.67 ± 4.58 | 5.51 ± 1.74 | 1.71 |
| Sulfamethazine | 0.9992 ± .0006 | 99.09 ± 8.80 | 10.91 ± 5.70 | 3.75 |
| Sulfamethoxazole | 0.9989 ± .0008 | 112.01 ± 8.15 | 11.35 ± 6.31 | 4.43 |
| Sulfisoxazole | 0.9986 ± .0009 | 93.08 ± 9.71 | 10.53 ± 4.74 | 5.61 |
| Sulfadimethoxine | 0.9984 ± .0016 | 102.99 ± 9.19 | 15.27 ± 8.14 | 8.89 |

TABLE 2

Compounds studied, (concentrations 62.5, 125, 250, 500, 1000 and 2000 ng/mL; 200 ng/mL sulfamerazine internal standard) correlation coefficients (+ or − standard deviation), percentage recovery, and inter- and intra-assay variabilities of the 8 sulfonamides isolated from spiked and pork samples. (SD = standard deviation, x = mean).

| COMPOUND | CORRELATION COEFFICIENT r ± SD, n = 5 | % RECOVERY x ± SD, n = 30 | INTERASSAY VARIABILITY % n = 30 | INTRA-ASSAY VARIABLITY %, n = 5 |
|---|---|---|---|---|
| Sulfanilamide | 0.9967 ± .0015 | 70.4 ± 12.7 | 11.22 ± 3.70 | 5.51 |
| Sulfathiazole | 0.9942 ± .0060 | 80.3 ± 11.1 | 10.81 ± 3.54 | 3.46 |
| Sulfadiazine | 0.9975 ± .0020 | 95.1 ± 15.1 | 7.16 ± 5.45 | 3.78 |
| Sulfamerazine | — | 78.1 ± 4.15 | 9.13 ± 4.80 | 4.82 |
| Sulfamethazine | 0.9991 ± .0006 | 84.7 ± 8.20 | 7.43 ± 4.28 | 4.01 |
| Sulfamethoxazole | 0.9989 ± .0005 | 95.7 ± 14.8 | 9.46 ± 5.36 | 3.89 |
| Sulfisoxazole | 0.9988 ± .0009 | 92.8 ± 11.8 | 10.01 ± 7.99 | 5.26 |
| Sulfadimethoxine | 0.9969 ± .0029 | 95.8 ± 12.4 | 13.28 ± 8.14 | 6.17 |

These data thus show that the sulfonamides were successfully eluted with methylene chloride, and that the sample extracts contained sulfonamide analates (62.5–2000 ng/g) which were free from interfering compounds when examined by HPLC utilizing photodiode array detection at 270 nm. Correlation coefficients of standard curves of sulfonamides isolated from spiked pork tissue ranged from 0.9942 (±0.006) to 0.9991 (±0.0006). Percentage recoveries (70.4–95.8%), intra- (3.46–6.17%) and inter-assay variabilities (4.04–14.05%) for the sulfonamides were indicative of a suitable quantitative method for the analysis of these compounds in a muscle tissue matrix.

EXAMPLES 23–29

An additional series of tests were conducted for the isolation and high performance liquid chromatographic (photodiode array, UV 270 nm) determination of sulfathiazole, sulfisoxazole, sulfamerazine, sulfamethazine, The results show that the present method overcomes some of the limitations of the classical methods. The sample, in this case infant formula (IF), was evenly distributed on a solid (C-18) support, thereby greatly increasing its surface area and exposing the entire sample to the extraction. Hexane was used to elute lipid material, while the more polar sulfonamides remaining on the column. Methylene chloride (DCM) was then used to elute the sulfonamides. The high percentage recoveries and small variabilities shown in Table 3 are a result of what can be envisioned as an exhaustive extraction process whereby a large volume of solvent is passed over an extremely thin layer of IF. The exact disbution of the IF components on the C-18 is not clear but it may involve an association of the lipid component with the lipophilic C-18 polymer and a simultaneous disruption of protein and/or micelle layers which align themselves with hydrophobic regions oriented toward the lipid, while hydrophilic regions extend outward. The hydrophilic regions can then associate with the water and other more polar constituents. This alignment of IF components on the C-18 packing is probably discontinuous in nature inasmuch as no difficulty was experienced in removing lipid material with the hexane wash.

The blank IF extract was relatively free of interfering compounds. A method blank contained no interfering compounds. This can be explained by the manner in which the sulfonamides were eluted from the column. The hexane wash removes lipids and other compounds, perhaps neutral chromophores, which could otherwise interfere with the analysis. Other more polar chromophores, which are not soluble in methylene chloride, remain on the column. Thus, one can selectively elute the compounds of interest while eliminating potentially interfering compounds.

mL) were blended with octadecylsilyl (C-18) derivatized silica (2 g). A column made from the sample-C-18 matrix was first washed with hexane (8 mL) following which the sulfonamides were eluted with methylene chloride (8 mL). As shown by reference to the data given in Table 4, the eluate contained sulfonamide analates which were free from interfering compounds when analyzed by high performance liquid chromatography (HPLC) utilizing UV detection (270 nm, photodiode array). Standard curve correlation coefficients (Range, $0.9983 \pm 0.0017$–$0.997 \pm 0.0001$), percentage recoveries ($73.1 \mp 7.36$–$93.68 \pm 2.73\%$), and the inter- ($3.98$–$9.62\%$) and intra-assay ($2.18$–$6.65\%$) variabilities, for the concentration range examined ($62.5$–$2000$ ng/g).

TABLE 4

Compounds studied (concentrations of 62.5, 125, 250, 500, 1000 and 2000 ng/mL; 250 ng/ml of sulfamerazine internal standard), correlation coefficients (+ or − standard deviation), percentage recovery and inter- and intra-assay variabilities of the 8 sulfonamides isolated from spiked milk samples. (SD = standard deviation, x = mean).

| COMPOUND | CORRELATION COEFFICIENT $r \pm SD, n = 5$ | % RECOVERY $x \pm SD, n = 30$ | INTERASSAY VARIABILITY %, n = 30 | INTRA-ASSAY VARIABLITIY %, n = 5 |
|---|---|---|---|---|
| Sulfanilamide | $0.9989 \pm .0006$ | $73.12 \pm 7.36$ | $5.57 \pm 3.29$ | 3.16 |
| Sulfathiazole | $0.9997 \pm .0001$ | $93.68 \pm 2.73$ | $6.64 \pm 1.12$ | 2.18 |
| Sulfadiazine | $0.9993 \pm .0005$ | $81.21 \pm 4.79$ | $4.76 \pm 2.92$ | 2.69 |
| Sulfamerazine | — | $81.96 \pm 4.59$ | $4.53 \pm 2.44$ | 2.66 |
| Sulfamethazine | $0.9997 \pm .0002$ | $92.67 \pm 5.57$ | $4.82 \pm 2.71$ | 2.29 |
| Sulfamethoxazole | $0.9995 \pm .0003$ | $89.43 \pm 8.28$ | $3.98 \pm 1.98$ | 5.08 |
| Sulfisoxazole | $0.9986 \pm .0008$ | $88.58 \pm 11.17$ | $8.12 \pm 3.09$ | 6.65 |
| Sulfadimethoxine | $0.9983 \pm .0017$ | $89.63 \pm 8.06$ | $9.62 \pm 3.32$ | 2.34 |

As a result of the cleanliness of the IF extracts a scale-up of this procedure allows for the determination of sulfonamide levels in the low ppb range. The minimal detectable limit for the compounds examined here, utilizing a photodioide array detector, was approximately 1.25 pg on column, which reflects the sensitivity characteristics of the detection system utilized in this study for these compounds. Because of the cleanliness of the extract, an increase in sensitivity could be achieved by increasing injection volume and/or dissolving the extract residue in a smaller final volume. Additionally, by extending the theoretical aspects of this method, it would appear clear that multi-residue sulfonamide determinations in other milk based products or liquids, as well as tissues or blood components, could be achieved with similar results.

The savings in terms of time and solvent, compared to classical extraction techniques, such as the method of Tishler (1968), make this procedure attractive. For example, the Tishler method requires 50 mL of milk which is extracted several times resulting in a minimum of 600 mL of extracting solvent that must be evaporated. Additional pH adjustments and washing is necessary before the sample is ready for analysis. The method of this invention requires a 0.5 mL sample, 8 mL of hexane and 8 mL of DCM and requires no extensive extract clean-up steps other than drying the DCM, centrifugation and filtering prior to analysis. Furthermore, use of this method results in extracts containing analates relatively free from interfering co-extractants which would aid in their detection by other more sensitive means, such as immunoassay techniques, by eliminating cross-reacting compounds.

EXAMPLES 30-37

Another series of tests were conducted for the isolation and liquid chromatographic determination of eight sulfonamides in milk. Spiked or blank milk samples (0.5

EXAMPLE 38

Tests were made for the isolation and liquid chromatographic determination of chloramphenicol in milk. Chloramphenicol spiked and blank milk samples (0.5 mL) were blended with octadecylsilyl (C-18) derivatized silica (2 g). The C-18/milk matrix was used to prepare a column which was washed with hexane (8 mL) followed by benzene (8 mL). Chloramphenicol was then eluted with ethylacetate (8 mL). The eluate contained chloramphenicol which was free from interfering compounds when analyzed by high performance liquid chromatography (HPLC) utilizing UV detection (278 nm, photodiode array). Linearity ($0.9996 \pm 0.0004$), average percentage recovery ($68.7 \pm 8.3\%$), inter- ($11.61 \pm 6.9\%$) and intra-assay ($1.35\%$) variabilities, for the concentration range examined (62.5–2000 ng/ml milk), were indicative of an acceptable method. The method was found to use small volumes of solvents, requires a limited number of sample manipulations, and no pH adjustments or backwashing of extracts, making this method attractive when compared to classical isolation procedures for chloramphenicol. Reference is made to Table 5.

TABLE 5

Chloramphenicol spiked milk sample (concentrations of 62.5, 125, 500, 1000, and 2000 ng/mL), standard curve correlation coefficients, percentage recovery, and inter- and intra-assay variabilities

| | |
|---|---|
| Correlation Coefficients (r; Mean ± SD, n = 5) | $0.9996 \pm 0.0004$ |
| % Recovery (n = 30) | $68.7 \pm 8.3\%$ |
| Inter-assay Variability (n = 30) | $11.61\% \pm 6.9\%$ |
| Intra-assay Variability (n = 5) | $1.35\%$ |

EXAMPLES 39-45

Tests were made for the isolation and liquid chromatographic determination of seven benzimidazole (thiabendazole, oxfendazole, para-hydroxyfenbendazole, fenbendazole sulfone, mebendazole, albendazole, and fenbendazole) anthelmintics in milk. Blank or benzimidazole spiked milk samples (0.5 mL) were blended with octadecylsilyl (C-18, 18% load, end-capped) derivatized silica packing material. A column made from the C-18/milk matrix was first washed with hexane (8 mL), following which the benzimidazoles were eluted with methylene chloride:ethyl acetate (1:2, v/v; 8 mL). The eluate contained benzimidazole analates which were free from interfering compounds as determined by UV detection (photodiode array, 290 nm). Correlation coefficients of standard curves for individual benzimidazoles isolated from spiked samples were linear (0.9893±0.0025 to 0.9988±0.0009) with percentage recoveries from 69.67±8.89% to 107.33±2.37% for the concentration range (31.25-2000 ng/mL) examined. The inter-assay variabilities were from 4.11±1.34% to 8.74±6.71 with intra-assay variabilities of from 2.9% to 5.73%. Reference is made to Table 6.

TABLE 6

Compounds examined (concentrations of 31.25, 62.5, 125, 250, 500, 1000 and 2000 ng/mL; mebendazole internal standard, 250 ng/mL), correlatin coefficients (+ or − standard deviation), percentage recovery, and inter- and intra-assay variabilities of the 7 benzimidazoles isolated from spiked milk samples. (SD = standard deviation, $\bar{x}$ = mean).

| COMPOUND | CORRELATION COEFFICIENT r ± SD, n = 5 | % RECOVERY x ± SD, n = 30 | INTERASSAY VARIABILITY %, n = 30 | INTRA-ASSAY VARIABLITY %, n = 5 |
|---|---|---|---|---|
| Thiabendazole | 0.9951 ± 0.0022 | 88.72 ± 5.81 | 7.46 ± 5.41 | 2.93 |
| Oxfendazole | 0.9893 ± 0.0025 | 107.33 ± 2.37 | 4.59 ± 1.79 | 2.61 |
| p-hydroxy-fenbendazole | 0.9979 ± 0.0008 | 94.42 ± 5.14 | 8.74 ± 6.71 | 1.97 |
| Fenbendazole Sulfone | 0.9984 ± 0.0008 | 100.23 ± 5.11 | 4.11 ± 4.14 | 5.73 |
| Mebendazole | Internal Standard | 101.33 ± 5.13 | 4.11 ± 1.34 | 3.68 |
| Albendazole | 0.9983 ± 0.0012 | 81.01 ± 6.81 | 10.14 ± 8.16 | 3.31 |
| Fenbendazole | 0.9988 ± 0.0009 | 69.67 ± 8.89 | 9.50 ± 7.47 | 2.90 |

EXAMPLE 46

A test was made for the isolation and pyrolysis gas chromatographic determination of chlorsulfuron in milk. Blank and chlorulfuron spiked milk samples were blended into C-18 (octadecylsilyl derivatized silica, ODS) packing material. A column made from the C-18/milk matrix was washed with hexane after which chlorsulfuron was eluted with dichloromethane (DCM). The DCM eluate contained chlorsulfuron which was free from interfering co-extractants when analyzed by gas chromatography utilizing a nitrogen/phosphorus detector. Standard curves for chlorsulfuron isolated from milk were linear (r=0.9920±0.004, n=5), with an average percentage recovery of 91.64±10.8%, over the concentration range examined (62.5-2000 ng/mL). The inter- and intra-assay variabilities were 11.59±7.47% and 6.20%, respectively. Specific reference is made to Table 7.

TABLE 7

Standard curve correlation coefficients, percentage recovery, inter- and intra-assay variabilities of chlorsulfuron isolated from spiked milk samples at concentrations of 62.5, 125, 250, 500, 1000 and 2,000 ng/mL, 2 uL injection volume (gas chromatography with nitrogen/phosphorus detector).

| | | |
|---|---|---|
| Correlation Coefficient | 0.9920 ± 0.004 | n = 5 |
| Percentage recovery | 91.64% ± 10.8% | n = 30 |
| Inter-assay Variability | 11.59% ± 7.47% | n = 30 |
| Intra-assay Variability | 6.20% | n = 5 |

The method, as shown by these data, represents a generic approach for the homogenization and extraction of tissues, and other complex matrices, for the isolation of drug residues, environmental contaminants and naturally occurring compounds. A specimen is dispersed, through blending onto a solid support to which is bound a lipid solubilizing polymer phase that will interact with the tissue to disrupt the matrix by dissolving and absorbing the cellular components of the tissue. The cellular components are then extracted, and eluted from a column prepared from the tissue and solid support.

A preferred class of solid supports found useful in the practice of this invention are desscribed as Sepralyte Chromatographic Sorbents, which are bonded silica sorbents produced, and marketed by Analytichem International, Inc. having a U.S.A. address at 24201 Frampton Avenue, Harbor City, Calif. 90710. Sepralyte Chromatographic Sorbents, as a family, are described in a current catalogue by Analytichem International, Inc., *Sample Preparation & Separation Science,* at Page 4, as a variety of chemically modified sorbents, specifically designed for ultraselective chemical separation. Sepralyte is silica gel which is covalently bonded to such non polar species as octadecyl, octyl, hexyl, butyl, ethyl, methyl, cyclohexyl, phenyl, diphenyl; polar species such as cyanopropyl, diol

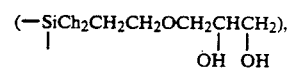

silica, aminopropyl, ethylenediamine-N-propyl; and ion-exchange species such as benzenesulfonylpropyl, sulfonylpropyl, carboxymethyl, diethylaminopropyl and trimethylaminopropyl.

It is apparent that the invention is susceptible to some variations, and modifications without departing the spirit and scope of the invention.

Having described the invention, what is claimed is:

1. A process for isolating a drug or drug metabolite from a biological specimen, comprising the steps of:
   (a) contacting the specimen with a particulate solid to which is bound a lipophilic material which exhibits lipid-solubilizing ability when thus bound;
   (b) grinding the specimen and the particulate solid for a time sufficient to disrupt at least some of the components of the specimen, and to disperse at least some of the components of the specimen into the lipophilic material; and
   (c) eluting the drug or drug metabolite from the particulate solid or lipophilic material with at least one solvent.

2. The process of claim 1 wherein the drug or drug metabolite is selected from the group consisting of an organophosphate, benzimidazole, antihelmintics, beta lactam antibiotics, sulfonamides, chloramphenicol, and chlorsulfuron.

3. The process of claim 1 wherein the biological specimen is a tissue, and the issue is ground under a pestle within a mortar.

4. The process of claim 1 wherein the solid to which the lipophilic material is bonded is silica.

5. The process of claim 4 wherein the lipophilic material comprises a chain containing up to about 30 carbon atoms.

6. The process of claim 1 wherein said eluting step comprises transferring the particulate solid to a column, and then contacting the particulate solid with at least one solvent.

7. The process of claim 6 wherein an acid, base, or salt is added to the column to modify the elution characteristics of the drug or drug metabolite.

8. The process of claim 1 wherein the eluted drug or drug metabolite is subjected to analysis without further clean-up of the specimen.

9. The process of claim 8 wherein the analysis is made by thin layer chromatography, immunoassay, gas chromatography, or high pressure liquid chromatography.

10. The process of claim 1 wherein the lipophilic material bound to the particulate solid so covalently bonded thereto, and is a non-polar, polar, or ionic species.

11. The process of claim 10 wherein the lipophilic material comprises a polar species which comprises R-silane, wherein R is selected from the group consisting of cyanopropyl, diol, silica, aminopropyl, and ethylenediamine-N-propyl.

12. The process of claim 10 wherein the lipophilic material comprises an ionic species which is selected from the group consisting of benzenesulfonylpropyl, sulfonylpropyl, carboxymethyl, diethylaminopropyl, and trimethylaminopropyl.

13. The process of claim 10 wherein the lipophilic material comprises a non-polar species which comprises a chain containing up to about 30 carbon atoms.

14. The process of claim 13 wherein the non-polar species comprises R-silane, wherein R is selected from the group consisting of octadecyl, octyl, hexyl, butyl, ethyl, methyl, cyclohexyl, phenyl, and diphenyl.

15. A process of isolating one or more components from a biological specimen, comprising the steps of:
   (a) contacting the specimen with a particulate solid to which is bound a lipophilic material which exhibits lipid-solubilizing ability when thus bound;
   (b) grinding the specimen and the particulate solid for a time sufficient to disrupt at least some of the components of the specimen, and to disperse at least some of the components of the specimen into the lipophilic material;
   (c) eluting at least one component from the particulate solid or lipophilic material with at least one solvent.

16. A process as recited in claim 15, wherein the specimen comprises cells.

17. A process as recited in claim 15, wherein the specimen comprises a tissue.

18. A process as recited in claim 15, wherein the specimen comprises milk.

19. A process as recited in claim 15, wherein a cellular component from the specimen is eluted in said eluting step.

20. A process as recited in claim 15, wherein the specimen comprises a tissue, and wherein the tissue is ground under a pestle within a mortar.

21. A process as recited in claim 15, wherein the solid to which the lipophilic material is bonded is silica.

22. A process as recited in claim 21, wherein the lipophilic material comprises a chain containing up to about 30 carbon atoms.

23. A process as recited in claim 15, wherein the lipophilic material bound to the particulate solid is covalently bonded thereto, and is a non-polar, polar, or ionic species.

24. A process as recited in claim 23, wherein the lipophilic material comprises a polar species which comprises R-silane, wherein R is selected from the group consisting of cyanopropyl, diol, silica, aminopropyl, and ethylenediamine-N-propyl.

25. A process as recited in claim 23, wherein the lipophilic material comprises an ionic species which is selected from the group consisting of benzenesulfonylpropyl, sulfonylpropyl, carboxymethyl, diethylaminopropyl, and trimethylaminopropyl.

26. A process as recited in claim 23, wherein the lipophilic material comprises a non-polar species which comprises a chain containing up to about 30 carbon atoms.

27. A process as recited in claim 26, wherein the non-polar species comprises R-silane, wherein R is selected from the group consisting of octadecyl, octyl, hexyl, butyl, ethyl, methyl, cyclohexyl, phenyl, and diphenyl.

28. A process as recited in claim 15, wherein said eluting step comprises transferring the particulate solid to a column, and then contacting the particulate solid with at least one solvent.

29. A process as recited in claim 28, wherein an acid, base, or salt is added to the column to modify the elution characteristics of at least one component of the specimen.

30. A process as recited in claim 29, wherein at least one eluted component is subjected to analysis without further clean-up of the specimen.

31. A process as recited in claim 30, wherein the analysis is made by thin layer chromatography, immunoassay, gas chromatography, or high pressure liquid chromatography.

* * * * *